US00PP34479P2

(12) United States Plant Patent
Danziger

(10) Patent No.: US PP34,479 P2
(45) Date of Patent: Aug. 2, 2022

(54) ***MIMULUS* PLANT NAMED 'DMIMMITIRD'**

(50) Latin Name: *Mimulus aurantiacus*
Varietal Denomination: 'DMIMMITIRD'

(71) Applicant: Danziger 'DAN' Flower Farm, Beit Dagan (IL)

(72) Inventor: Gavriel Danziger, Beit Dagan (IL)

(73) Assignee: Danziger "Dan" Flower Farm

( * ) Notice: Subject to any disclaimer, the term of this patent is extended or adjusted under 35 U.S.C. 154(b) by 0 days.

(21) Appl. No.: 17/579,880

(22) Filed: Jan. 20, 2022

(51) Int. Cl.
*A01H 5/02* (2018.01)

(52) U.S. Cl.
USPC ..... Plt./454

(58) Field of Classification Search
USPC ..... Plt./454
See application file for complete search history.

*Primary Examiner* — Annette H Para
(74) *Attorney, Agent, or Firm* — Cassandra Bright

(57) ABSTRACT

A new and distinct cultivar of *Mimulus* plant named 'DMIMMITIRD' is disclosed, characterized by early flowering plants with dark green foliage and abundant flowering. Foliage is uniquely less sticky than typical of *Mimulus aurantiacus*. The new variety is a *Mimulus*, normally produced as an outdoor garden or container plant.

2 Drawing Sheets

Latin name of the genus and species: *Mimulus aurantiacus*.
Variety denomination: 'DMIMMITIRD'.

BACKGROUND OF THE INVENTION

The new *Mimulus* cultivar is the product of a planned breeding program conducted by the inventor, Gavriel Danziger, in Moshav Mishmar Hashiva, Israel. The objective of the breeding program was to produce new *Mimulus* varieties for ornamental commercial applications. The open pollination resulting in this new variety was made in July of 2015.

The seed parent is an unpatented, unnamed proprietary *Mimulus aurantiacus*. The pollen parent is a different unpatented, unnamed proprietary *Mimulus aurantiacus*. The new variety was selected in July of 2016 by the inventor in a group of seedlings resulting from the 2015 crossing, in a research greenhouse in Moshav Mishmar Hashiva, Israel.

Asexual reproduction of the new cultivar has been performed by vegetative cuttings. This was first performed at a research greenhouse in Moshav Mishmar Hashiva, Israel in July of 2016, and has shown that the unique features of this cultivar are stable and reproduced true to type in multiple successive generations.

SUMMARY OF THE INVENTION

The cultivar 'DMIMMITIRD' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DMIMMITIRD' These characteristics in combination distinguish 'DMIMMITIRD' as a new and distinct *Mimulus* cultivar:

1. Dark green foliage.
2. Foliage with reduced stickiness.
3. Abundant flowering.
4. Early flowering.

PARENTAL COMPARISON

Plants of the new cultivar 'DMIMMITIRD' are similar to plants of the seed parent in most horticultural characteristics, however, plants of the new cultivar 'DMIMMITIRD' differ in the following;

1. Plants of the new variety are more compact than plants of the seed parent variety.
2. Plants of the new variety flower more abundantly than the seed parent variety.
3. Flowers of the new variety are darker red than flowers of the seed parent.
4. Foliage of the new variety is smaller than foliage of the seed parent.
5. Foliage of the new variety is less sticky than foliage of the seed parent.

Plants of the new cultivar 'DMIMMITIRD' are similar to plants of the pollen parent in most horticultural characteristics, however, plants of the new cultivar 'DMIMMITIRD' differ in the following;

1. Plants of the new variety are more compact than plants of the pollen parent variety.
2. Plants of the new variety flower more abundantly than the pollen parent variety.
3. Flowers of the new variety are red; flowers of the pollen parent are orange.
4. Foliage of the new variety is shorter and wider than foliage of the pollen parent.
5. Foliage of the new variety is less sticky than foliage of the pollen parent.

COMMERCIAL COMPARISON

Plants of the new cultivar 'DMIMMITIRD' can be compared to the commercial variety *Mimulus aurantiacus* 'Curious Orange', unpatented. 'These varieties are similar in most horticultural characteristics;

1. Foliage of the new variety is lighter in color than foliage of this comparator variety.
2. Plants of the new variety begin flowering earlier than plants of this comparator.
3. The new variety produces red flowers; this comparator produces orange flowers.
4. Foliage of the new variety is smaller than foliage of this comparator.

Plants of the new cultivar 'DMIMMITIRD' can be compared to the commercial variety *Mimulus aurantiacus* 'Curious Red', unpatented. 'These varieties are similar in most horticultural characteristics;

1. Plants of the new variety begin flowering earlier than plants of this comparator.
2. The new variety produces darker red flowers than this comparator.
3. Foliage of the new variety is smaller than foliage of this comparator.

BRIEF DESCRIPTION OF THE FIGURES

The accompanying photographs illustrate the overall appearance of the new *Mimulus aurantiacus* 'DMIMMITIRD' showing the colors as true as is reasonably possible with colored reproductions of this type. Colors in the photographs may differ slightly from the color values cited in the detailed botanical description which accurately describes the color of 'DMIMMITIRD'.

DETAILED BOTANICAL DESCRIPTION

Figure 1:
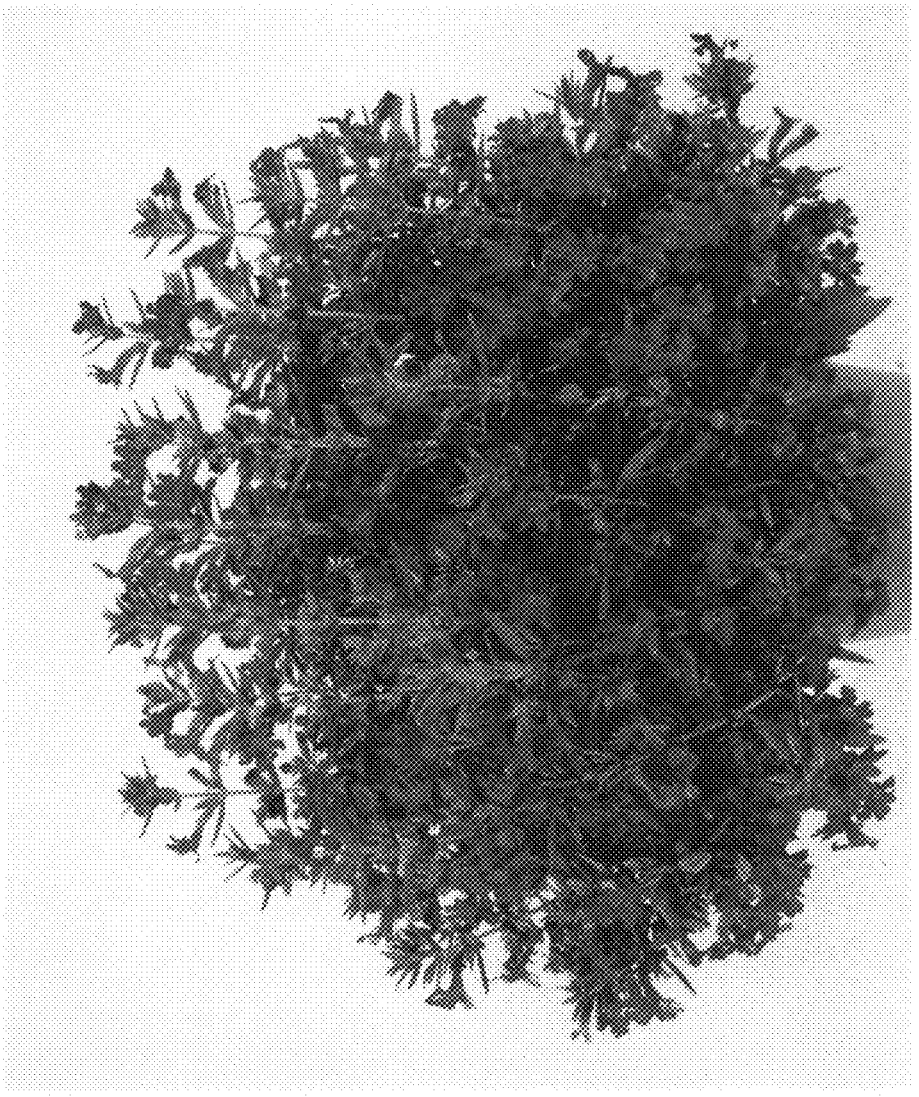
FIG. 1 shows a side view perspective of a typical flowering plant of 'DMIMMITIRD', at approximately 75 days old.
Figure 2:
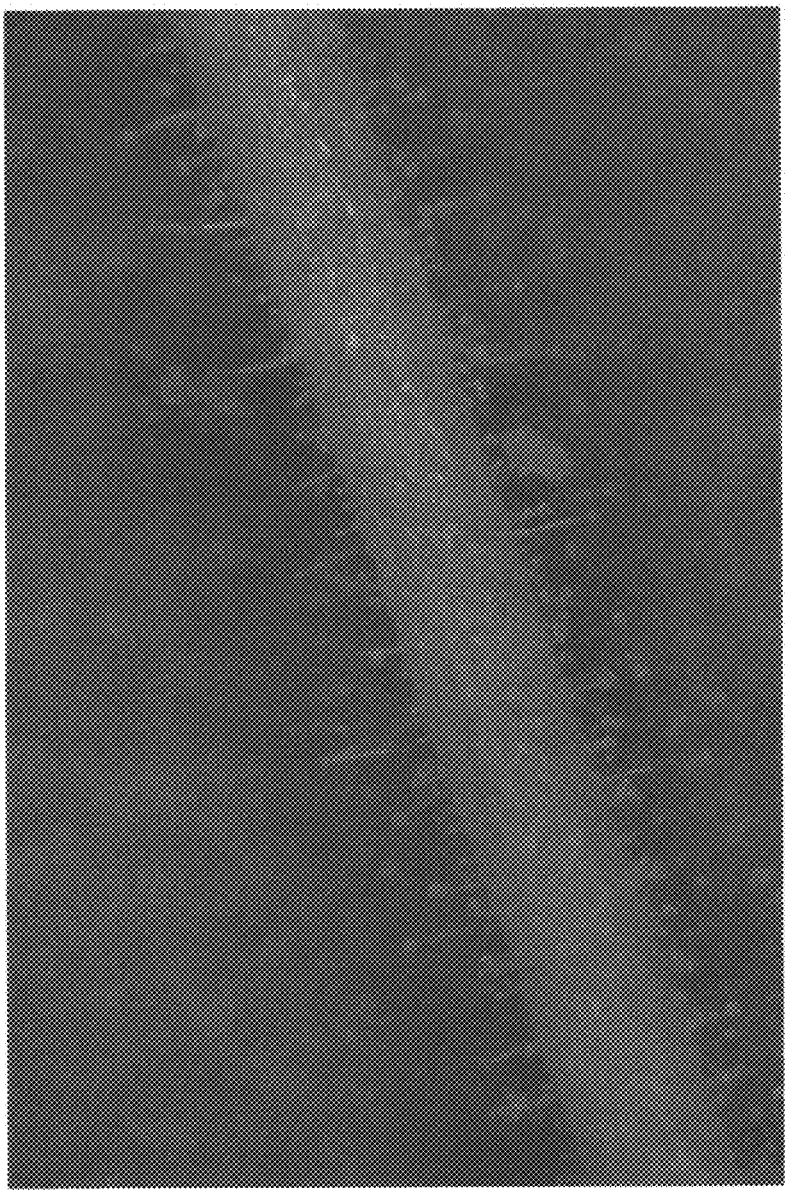
FIG. 2 shows a close-up view of a typical leaf of 'DMIMMITIRD', with less sticky substance than normally found on stems of *Mimulus aurantiacus*.

'DMIMMITIRD' has not been tested and observed under all possible environmental conditions. The phenotype of the new cultivar may vary with variations in environment such as temperature, light intensity, frequency of fertilization, composition of fertilizer, acetylene treatment, day length and humidity, without any change in the genotype of the plant.

For example, substantial differences in plant height and diameter, number of leaves, and size of inflorescences can result depending on the growing conditions. Typically, these plants are produced outdoors, and variations in temperature and humidity can produce different results.

The aforementioned photographs, together with the following observations, measurements and values describe the new *Mimulus* 'DMIMMITIRD' as grown in a greenhouse in Mishmar Hashiva, Israel, during Summer, under conditions which closely approximate those generally used in commercial practice. Plants of 'DMIMMITIRD' were grown with day temperatures ranging from about 25° C. to 35° C. and night temperatures ranging from about 10° C. to 15° C.

Color references are made to The Royal Horticultural Society Colour Chart (RHS), 2005 mini edition, except where general colors of ordinary significance are used. Color values were taken under daylight conditions in a greenhouse Mishmar Hashiva, Israel . The age of the plants of 'DMIMMITIRD' described is about 75 days from planting a rooted cutting.

Botanical classification: *Mimulus aurantiacus* 'DMIMMITIRD'.

PROPAGATION

Type of propagation typically used: Vegetative cuttings.
Time to initiate roots: 21 to 30 days at approximately 15° C.

PLANT

Growth habit: Upright flowering perennial subshrub.
Pot size of plant described: 12 cm.
Height: Approximately 36 cm to top of flowers.
Plant spread: 16 cm.
Growth Rate: Moderate.
Quantity of primary lateral branches: Average 6.
Characteristics of primary lateral branches:
- *Length.*—Average 14 cm.
- *Diameter.*—4 mm.
- *Shape.*—Cylindrical.
- *Color.*—Near RHS Yellow-Green 144C.
- *Texture.*—Puberulous, glandular hairs.
- *Strength.*—Moderate, flexible.

Internode length: Average 1.5 cm.

FOLIAGE

Leaf:
- *Arrangement.*—Opposite.
- *Quantity.*—Approximately 22 per branch.
- *Average length.*—3.6 cm.
- *Average width.*—1 cm.
- *Shape of blade.*—Lanceolate.
- *Apex.*—Acute.
- *Base.*—Cuneate.
- *Margin.*—Serrulate.
- *Texture of top surface.*—Muricate.
- *Texture of bottom surface.*—Glandular hairs.
- *Aspect.*—Concave.
- *Stickiness of foliage sticky.*—Moderate. Less than typical for species.
- *Color.*—Young foliage upper side: Near RHS Green N137A. Young foliage under side: Near RHS Green 138B. Mature foliage upper side: Near RHS Green 137C. Mature foliage under side: Near RHS Green 138B.
- *Venation.*—Type: Pinnate. Venation color upper side: Near RHS Green N137A. Venation color under side: Near RHS Yellow-Green 144D.
- *Petiole.*—Not present, sessile.

FLOWER

Natural flowering season: Spring to Autumn in Israel.
Days to flowering from rooted cutting: 53 days.
Rate of flower opening: 4 to 7 days from bud to fully opened flower.
Flower longevity on plant: 7 to 10 days.
Persistent or self-cleaning: Persistent.
Bud:
- *Shape.*—Campanulate (Bell Shaped).
- *Length.*—1-1.5 cm.
- *Diameter.*—0.5-0.7 cm.
- *Color.*—Near RHS Yellow-Green 144A to 144B.

Corolla:
- *Petals.*—Number: 5. Length: Central petals: 1.5 cm Lateral petals: 2 cm. Width: Central petals: 1 cm Lateral petals: 1.5 cm. Shape: Wide deltate, notched. Facing/Aspect: Outward facing, about 45 degrees to stem. Margin: Entire. Texture: Stringose, suede like. Color: When opening: Upper surface: Near RHS Red 53A.
- *Lower surface.*—Near Yellow-Orange 22D heavily flushed Red-Purple 71A. Fully opened: Upper surface: Near RHS Red 46B.
- *Lower surface.*—Near Orange 26D heavily flushed Red-Purple 71B.
- *Lower petal* (*lower lip*).—Length: 1.5 cm. Width: 1 cm. Shape: Wide deltate, notched. Apex shape: Notched. Color: Upper surface: Near RHS Red 46B. Lower surface: Near RHS Orange 26D.
- *Palate.*—Length: 5 mm. Width: 7 mm. Color: Near RHS Orange 26A. Texture: Glandular hairs.

*Throat.*—Length: 18 mm. Width: 9 mm. Texture: Glabrous. Pubescence: None.
*Spur.*—Not present.

Calyx:
*Form.*—Fused, tubular.
*Length.*—12 mm.
*Diameter.*—6 mm.
*Apex.*—Acute.
*Margin.*—Entire.
*Texture.*—Glandular hairs.
*Color.*—Upper surface: Near RHS Yellow-Green 144A to 144B. Lower surface: Near RHS Yellow-Green 144B RHS.

Pedicel:
*Strength.*—Strong.
*Aspect.*—Straight, 45° from stem.
*Length.*—3-5 mm.
*Diameter.*—1 mm.
*Texture.*—Glandular hairs.
*Color.*—Near RHS Yellow-Green 144B RHS.

Fragrance: Typical lightly musky.

REPRODUCTIVE ORGANS

Stamens:
*Number* (*per flower*).—4.
*Filament length.*—2 to 2.5 cm.
*Anthers.*—Shape: Y-shaped. Length: 1 mm. Color: Near RHS Yellow 13B.

Pollen:
*Color.*—Near RHS Yellow 13B.
*Amount.*—Moderate.

Pistils:
*Quantity per flower.*—1.
*Length.*—2.5 mm.
*Style.*—Length: 2.2 mm. Color: Near RHS Green-Yellow 1D.
*Stigma.*—Shape: Rhomboidal. Color: Near RHS Green-Yellow 1D.

OTHER CHARACTERISTICS

Seeds and fruits: Elongated fruits, fine dustlike seeds.

Disease/pest resistance: Neither resistance nor susceptibility to normal diseases and pests of *Mimulus* has been observed.

Temperature tolerance: USDA Zones 7-11.

Drought tolerance: Some drought tolerance observed, strongest when established.

What is claimed is:

1. A new and distinct cultivar of *Mimulus* plant named 'DMIMMITIRD' as herein illustrated and described.

* * * * *